(12) United States Patent
Xiong

(10) Patent No.: US 8,112,241 B2
(45) Date of Patent: Feb. 7, 2012

(54) METHODS AND SYSTEMS FOR GENERATING AN INSPECTION PROCESS FOR A WAFER

(75) Inventor: Yan Xiong, Sunnyvale, CA (US)

(73) Assignee: KLA-Tencor Corp., San Jose, CA (US)

( * ) Notice: Subject to any disclaimer, the term of this patent is extended or adjusted under 35 U.S.C. 154(b) by 406 days.

(21) Appl. No.: 12/403,905

(22) Filed: Mar. 13, 2009

(65) Prior Publication Data

US 2010/0235134 A1    Sep. 16, 2010

(51) Int. Cl.
   *G01R 27/28*    (2006.01)
   *G06K 9/00*    (2006.01)
(52) U.S. Cl. .................. 702/117; 382/144; 702/123
(58) Field of Classification Search ............ 702/33, 702/35, 117, 182, 183, 187, 123; 250/310; 356/237.3, 237.4, 394; 382/141, 144, 145; 700/90, 108, 109, 110; 703/104
   See application file for complete search history.

(56) References Cited

U.S. PATENT DOCUMENTS

| | | |
|---|---|---|
| 3,495,269 A | 2/1970 | Mutschler et al. |
| 3,496,352 A | 2/1970 | Jugle |
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano et al. |
| 4,633,504 A | 12/1986 | Wihl |
| 4,641,353 A | 2/1987 | Kobayashi |
| 4,641,967 A | 2/1987 | Pecan |
| 4,734,721 A | 3/1988 | Boyer et al. |
| 4,748,327 A | 5/1988 | Shinozaki et al. |

(Continued)

FOREIGN PATENT DOCUMENTS

EP    0032197    7/1981

(Continued)

OTHER PUBLICATIONS

International Search Report and Written Opinion for PCT/US2010/026559 mailed Oct. 20, 2010.

(Continued)

*Primary Examiner* — John H Le
(74) *Attorney, Agent, or Firm* — Ann Marie Mewherter

(57) ABSTRACT

Methods and systems for generating an inspection process for a wafer are provided. One computer-implemented method includes separately determining a value of a local attribute for different locations within a design for a wafer based on a defect that can cause at least one type of fault mechanism at the different locations. The method also includes determining a sensitivity with which defects will be reported for different locations on the wafer corresponding to the different locations within the design based on the value of the local attribute. In addition, the method includes generating an inspection process for the wafer based on the determined sensitivity. Groups may be generated based on the value of the local attribute thereby assigning pixels that will have at least similar noise statistics to the same group, which can be important for defect detection algorithms. Better segmentation may lead to better noise statistics estimation.

28 Claims, 2 Drawing Sheets

U.S. PATENT DOCUMENTS

| | | |
|---|---|---|
| 4,758,094 A | 7/1988 | Wihl |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,459,520 A | 10/1995 | Sasaki |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edger et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,415,421 B2 | 7/2002 | Anderson et al. |
| 6,445,199 B1 | 9/2002 | Satya et al. |
| 6,451,690 B1 | 9/2002 | Matsumoto |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk et al. |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser |
| 6,751,519 B1 | 6/2004 | Satya et al. |
| 6,753,954 B2 | 6/2004 | Chen |
| 6,757,645 B2 | 6/2004 | Chang |
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |

| Patent No. | Date | Inventor |
|---|---|---|
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie |
| 6,859,746 B1 | 2/2005 | Stirton |
| 6,879,924 B2 | 4/2005 | Ye et al. |
| 6,882,745 B2 | 4/2005 | Brankner |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski |
| 7,124,386 B2 | 10/2006 | Smith |
| 7,133,548 B2 | 11/2006 | Kenan et al. |
| 7,135,344 B2 | 11/2006 | Nehmadi |
| 7,136,143 B2 | 11/2006 | Smith |
| 7,152,215 B2 | 12/2006 | Smith |
| 7,162,071 B2 | 1/2007 | Hung et al. |
| 7,171,334 B2 | 1/2007 | Gassner |
| 7,174,520 B2 | 2/2007 | White |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,379,175 B1 | 5/2008 | Stokowski et al. |
| 7,383,156 B2 | 6/2008 | Matsusita et al. |
| 7,386,839 B2 | 6/2008 | Golender et al. |
| 7,418,124 B2 | 8/2008 | Peterson et al. |
| 7,424,145 B2 | 9/2008 | Horie et al. |
| 7,676,077 B2 | 3/2010 | Kulkarni et al. |
| 7,738,093 B2 | 6/2010 | Alles et al. |
| 7,739,064 B1 | 6/2010 | Ryker et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0164065 A1 | 11/2002 | Cai et al. |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0014146 A1 | 1/2003 | Fujii |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher |
| 2003/0048939 A1 | 3/2003 | Lehman |
| 2003/0057971 A1 | 3/2003 | Nishiyama et al. |
| 2003/0086081 A1 | 5/2003 | Lehman |
| 2003/0094572 A1 | 5/2003 | Matsui et al. |
| 2003/0098805 A1 | 5/2003 | Bizjak |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0228714 A1 | 12/2003 | Smith |
| 2003/0229410 A1 | 12/2003 | Smith |
| 2003/0229412 A1 | 12/2003 | White |
| 2003/0229868 A1 | 12/2003 | White |
| 2003/0229875 A1 | 12/2003 | Smith |
| 2003/0229880 A1 | 12/2003 | White |
| 2003/0229881 A1 | 12/2003 | White |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0174506 A1 | 9/2004 | Smith |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0062962 A1 | 3/2005 | Fairley |
| 2005/0117796 A1 | 6/2005 | Matsui et al. |
| 2005/0132306 A1 | 6/2005 | Smith |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner |
| 2006/0000964 A1 | 1/2006 | Ye et al. |
| 2006/0036979 A1 | 2/2006 | Zurbrick et al. |
| 2006/0048089 A1 | 3/2006 | Schwarzbaned |
| 2006/0051682 A1 | 3/2006 | Hess et al. |
| 2006/0062445 A1 | 3/2006 | Verma et al. |
| 2006/0082763 A1 | 4/2006 | The et al. |
| 2006/0159333 A1 | 7/2006 | Ishikawa |
| 2006/0161452 A1 | 7/2006 | Hess et al. |
| 2006/0193506 A1 | 8/2006 | Dorphan et al. |
| 2006/0193507 A1 | 8/2006 | Sali et al. |
| 2006/0236294 A1 | 10/2006 | Saidin |
| 2006/0236297 A1 | 10/2006 | Melvin et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |

| | | | |
|---|---|---|---|
| 2006/0291714 | A1 | 12/2006 | Wu et al. |
| 2006/0292463 | A1 | 12/2006 | Best et al. |
| 2007/0002322 | A1 | 1/2007 | Borodovsky et al. |
| 2007/0019171 | A1 | 1/2007 | Smith |
| 2007/0031745 | A1 | 2/2007 | Ye et al. |
| 2007/0032896 | A1 | 2/2007 | Ye et al. |
| 2007/0035322 | A1 | 2/2007 | Kang et al. |
| 2007/0035712 | A1 | 2/2007 | Gassner et al. |
| 2007/0035728 | A1 | 2/2007 | Kekare et al. |
| 2007/0052963 | A1 | 3/2007 | Orbon |
| 2007/0064995 | A1 | 3/2007 | Oaki et al. |
| 2007/0133860 | A1 | 6/2007 | Lin |
| 2007/0156379 | A1 | 7/2007 | Kulkarni et al. |
| 2007/0230770 | A1 | 10/2007 | Kulkarni et al. |
| 2007/0248257 | A1 | 10/2007 | Bruce et al. |
| 2007/0280527 | A1 | 12/2007 | Almogy et al. |
| 2007/0288219 | A1 | 12/2007 | Zafar et al. |
| 2008/0013083 | A1 | 1/2008 | Kirk et al. |
| 2008/0049994 | A1 | 2/2008 | Rognin et al. |
| 2008/0072207 | A1 | 3/2008 | Verma et al. |
| 2008/0081385 | A1 | 4/2008 | Marella et al. |
| 2008/0163140 | A1 | 7/2008 | Fouquet et al. |
| 2008/0167829 | A1 | 7/2008 | Park et al. |
| 2008/0250384 | A1 | 10/2008 | Duffy et al. |
| 2008/0295047 | A1 | 11/2008 | Nehmadi et al. |
| 2008/0304056 | A1 | 12/2008 | Alles et al. |
| 2009/0016595 | A1 | 1/2009 | Peterson et al. |
| 2009/0024967 | A1 | 1/2009 | Su et al. |
| 2009/0037134 | A1 | 2/2009 | Kulkarni et al. |
| 2009/0041332 | A1 | 2/2009 | Bhaskar et al. |
| 2009/0043527 | A1 | 2/2009 | Park et al. |
| 2009/0055783 | A1 | 2/2009 | Florence et al. |
| 2009/0080759 | A1 | 3/2009 | Bhaskar et al. |
| 2009/0210183 | A1 | 8/2009 | Rajski et al. |
| 2009/0257645 | A1 | 10/2009 | Chen et al. |

FOREIGN PATENT DOCUMENTS

| | | |
|---|---|---|
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1480034 | 11/2004 |
| EP | 1696270 | 8/2006 |
| JP | 2002-071575 | 3/2002 |
| JP | 2002-365235 | 12/2002 |
| JP | 2004-045066 | 2/2004 |
| KR | 10-2001-0037026 | 5/2001 |
| KR | 10-2001-0101697 | 11/2001 |
| KR | 1020030055848 | 7/2003 |
| KR | 10-2005-0092053 | 9/2005 |
| KR | 10-2006-0075691 | 7/2006 |
| WO | WO 98/57358 | 12/1998 |
| WO | WO 99/22310 | 5/1999 |
| WO | WO 99/25004 | 5/1999 |
| WO | WO 99/38002 | 7/1999 |
| WO | WO 99/41434 | 8/1999 |
| WO | WO 99/59200 | 11/1999 |
| WO | WO 00/03234 | 1/2000 |
| WO | WO 00/36525 | 6/2000 |
| WO | WO 00/55799 | 9/2000 |
| WO | WO 00/68884 | 11/2000 |
| WO | WO 00/70332 | 11/2000 |
| WO | WO 01/09566 | 2/2001 |
| WO | WO 01/40145 | 6/2001 |
| WO | WO 03/104921 | 12/2003 |
| WO | WO 2004/027684 | 4/2004 |
| WO | WO 2006/063268 | 6/2006 |
| WO | 2010/093733 | 8/2010 |

OTHER PUBLICATIONS

Allan et al., "Critical Area Extraction for Soft Fault Estimation," IEEE Transactions on Semiconductor Manufacturing, vol. 11, No. 1, Feb. 1998.

Barty et al., "Aerial Image Microscopes for the inspection of defects in EUV masks," Proceedings of SPIE, vol. 4889, 2002, pp. 1073-1084.

Budd et al., "A New Mask Evaluation Tool, the Microlithography Simulation Microscope Aerial Image Measurement System," SPIE vol. 2197, 1994, pp. 530-540.

Cai et al., "Enhanced Dispositioning of Reticle Defects Using the Virtual Stepper With Automoated Defect Severity Scoring," Proceedings of the SPIE, vol. 4409, Jan. 2001, pp. 467-478.

Comizzoli, "Uses of Corono Discharges in the Semiconfuctor Industry," J. Electrochem. Soc., 1987, pp. 424-429.

Contactless Electrical Equivalent Oxide Thickness Measurement, IBM Technical Disclosure Bulletin, vol. 29, No. 10, 1987, pp. 4622-4623.

Contactless Photovoltage vs. Bias Method for Determining Flat-Band Voltage, IBM Technical Disclosure Bulletin, vol. 32, vol. 9A, 1990, pp. 14-17.

Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.

Diebold et al., "Characterization and production metrology of thin transistor gate oxide films," Materials Science in Semiconductor Processing 2, 1999, pp. 103-147.

Dirksen et al., "Impact of high order aberrations on the performance of the aberration monitor," Proc. of SPIE vol. 4000, Mar. 2000, pp. 9-17.

Dirksen et al., "Novel aberration monitor for optical lithography," Proc. of SPIE vol. 3679, Jul. 1999, pp. 77-86.

Garcia et al., "New Die to Database Inspection Algorithm for Inspection of 90-nm Node Reticles," Proceedings of SPIE, vol. 5130, 2003, pp. 364-374.

Granik et al., "Sub-resolution process windows and yield estimation technique based on detailed full-chip CD simulation," Mentor Graphics, Sep. 2000, 5 pages.

Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.

Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992.

Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.

International Search Report for PCT/US2003/21907 mailed Jun. 7, 2004.

International Search Report for PCT/US2004/040733 mailed Dec. 23, 2005.

International Search Report and Written Opinion for PCT Appln. No. PCT/US08/050397 dated Jul. 11, 2008.

International Search Report and Written Opinion for PCT Appln. No. PCT/US06/61113 dated Jul. 16, 2008.

International Search Report and Written Opinion for PCT/US2008/062873 mailed Aug. 12, 2008.

International Search Report and Written Opinion for PCT Appln. No. PCT/US2008/063008 dated Aug. 18, 2008.

International Search Report for PCT/US2008/62875 mailed Sep. 10, 2008.

International Search Report and Written Opinion for PCT Appln. No. PCT/US06/61112 dated Sep. 25, 2008.

International Search Report for PCT/US2008/70647 mailed Dec. 16, 2008.

International Search Report and Written Opinion for PCT/US2008/073706 mailed Jan. 29, 2009.

International Search Report and Written Opinion for PCT/US2008/072636 mailed Jan. 29, 2009.

Karklin et al., "Automatic Defect Severity Scoring for 193 nm Reticle Defect Inspection," Proceedings of SPIE—The International Society for Optical Engineering, 2001, vol. 4346, No. 2, pp. 898-906.

Lo et al., "Identifying Process Window Marginalities of Reticle Designs for 0.15/0.13 µm Technologies," Proceedings of SPIE vol. 5130, 2003, pp. 829-837.

Lorusso et al. "Advanced DFM Applns. Using design-based metrology on CDSEM," SPIE vol. 6152, Mar. 27, 2006.

Lu et al., "Application of Simulation Based Defect Printability Analysis for Mask Qualification Control," Proceedings of SPIE, vol. 5038, 2003, pp. 33-40.

Mack, "Lithographic Simulation: A Review," Proceedings of SPIE vol. 4440, 2001, pp. 59-72.

Martino et al., "Application of the Aerial Image Measurement System (AIMS(TM)) to the Analysis of Binary Mask Imaging and Resolution Enhancement Techniques," SPIE vol. 2197, 1994 pp. 573-584.

Miller, "A New Approach for Measuring Oxide Thickness," Semiconductor International, Jul. 1995, pp. 147-148.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed.,© Cambridge University Press 1988, 1992, p. 683.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Schroder et al., Corono-Oxide-Semiconductor Device Characterization, 1998, Solid-State Electronics, vol. 42, No. 4, pp. 505-512.

Schroder, "Surface voltage and surface photovoltage: history, theory and applications," Measurement Science and Technology, vol. 12, 2001, pp. R16-31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

U.S. Appl. No. 10/677,445, (Horner et al.) entitled Methods for Non-Contacting Differential Voltage Measurements filed on Oct. 2, 2003.

U.S. Appl. No. 10/778,752, (Mack et al.) entitled Methods for Improved Monitor and Control of Lithography Processes filed on Feb. 13, 2004.

U.S. Appl. No. 11/154,310, (Verma et al.) entitled Computer-Implemented Methods, Simulation Engines and Systems for filed on Jun. 16, 2005.

U.S. Appl. No. 12/102,343, (Chen et al.) entitled Methods and Systems for Determining a Defect Criticality Index for Defects on Wafers filed on Apr. 14, 2008.

U.S. Appl. No. 12/394,752, (Xiong et al.) entitled Methods and Systems for Classifying Defects Detected on a Reticle filed on Feb. 27, 2009.

U.S. Appl. No. 60/418,887, (Su et al.) entitled Methods and Systems for Inspecting Reticles Using Aerial Imaging and Die-To-Database Detection filed on Oct. 15, 2002.

U.S. Appl. No. 60/418,994, (Stokowski et al.) entitled Methods and Systems for Reticle Inspection and Defect Review Using Aerial Imaging filed on Oct. 15, 2002.

U.S. Appl. No. 60/419,028, (Stokowski et al.) entitled Methods and Systems for Inspecting Reticles Using Aerial Imaging at Off-Stepper Wavelengths filed on Oct. 15, 2002.

U.S. Appl. No. 60/451,707, (Howard et al.) entitled Methods and Systems for Classifying and Analyzing Defects on Reticles filed on Mar. 4, 2003.

U.S. Appl. No. 60/526,881, (Hess et al.) entitled Designer Intent filed on Dec. 4, 2003.

U.S. Appl. No. 60/609,670, (Preil et al.) entitled Methods, Systems, and Carrier Media for Evaluating Reticle Layout Data filed on Sep. 14, 2004.

U.S. Appl. No. 60/681,095, (Nehmadi et al.) entitled Methods in Mask and Process Qualification filed on May 13, 2005.

U.S. Appl. No. 60/684,360, (Nehmadi et al.) entitled Design-Based Inspection filed on May 24, 2005.

U.S. Appl. No. 60/738,290, (Kulkarni et al.) entitled Methods and Systems for Utilizing Design Data in Combination With Inspection Data filed on Nov. 18, 2005.

U.S. Appl. No. 60/772,418, (Kirk et al.) entitled Methods and Systems for Determining a Characteristic of a Wafer filed on Feb. 9, 2006.

Verkuil et al., "A Contactless Alternative to MOS Charge Measurements by Means of a Corona-Oxide-Semiconductor (COS) Technique, "Electrochem. Soc. Extended Abstracts, 1988, vol. 88-1, No. 169, pp. 261-262.

Verkuil, "Rapid Contactless Method for Measuring Fixed Oxide Charge ASsociated with Silicon Processing," IBM Technical Disclousre Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/SEMI Advanced Manufacturing Conference, pp. 29-35.

Volk et al., "Investigation of Smart Inspection of Critical Layer Reticles using Additional Designer Data to Determine Defect Significance," Proceeings of SPIE vol. 5256, 2003, pp. 489-499.

Weinberg, "Tunneling of Electrons from Si into Thermally Grown SiO2," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 un Lithography," SPIE vol. 1604, 1991, pp. 106-117.

U.S. Appl. No. 10/793,599, filed Mar. 4, 2004 by Howard et al.

U.S. Appl. No. 11/139,151, filed Feb. 10, 2005 by Volk.

International Search Report for PCT/US2008/066328 mailed Oct. 1, 2009.

O'Gorman et al., "Subpixel Registration Using a Concentric Ring Fiducial," Proceedings of the International Conference on Pattern Recognition, vol. II, Jun. 16, 1990, pp. 249-253.

Huang et al., "Using Design Based Binning to Improve Defect Excursion Control for 45nm Production," IEEE, International Symposium on Semiconductor Manufacturing, Oct. 2007, pp. 1-3.

Sato et al., "Defect Criticality Index (DCI): A new methodology to significantly improve DOI sampling rate in a 45nm production environment," Metrology, Inspection, and Process Control for Microlithography XXII, Proc. of SPIE vol. 6922, 692213 (2008), pp. 1-9.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

METHODS AND SYSTEMS FOR GENERATING AN INSPECTION PROCESS FOR A WAFER

BACKGROUND OF THE INVENTION

1. Field of the Invention

The present invention generally relates to methods and systems for generating an inspection process for a wafer. Certain embodiments relate to determining a sensitivity of an inspection process based on local attributes determined for different locations within a design for a wafer.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Most types of inspection systems have adjustable sensitivity (or defect detection) parameters such that different parameters can be used to detect different defects or avoid sources of unwanted (nuisance) events. Although adjustable sensitivity parameters present significant advantages to a semiconductor device manufacturer, inspection systems are essentially useless if inappropriate sensitivity parameters are used for an inspection process. Although using appropriate sensitivity parameters can have a dramatic effect on the results of inspection, it is conceivable that many inspection processes are currently being performed with incorrect or non-optimized sensitivity parameters. In addition, it may be advantageous to use different sensitivity parameters to detect defects in different portions of the wafer (e.g., based on information about the device being formed on the wafer or information about the characteristics of the light from the wafer). However, many methods and systems for determining different sensitivity parameters for different portions of a wafer are disadvantageous. For example, the patterned features being printed on wafers are becoming more difficult to image by currently used inspection systems. Therefore, it is difficult to use information about the device being formed on the wafer obtained by scanning the wafer to change the sensitivity depending on the portion of the device in which the defects are being detected.

Accordingly, it would be advantageous to develop methods and systems for generating an inspection process for a wafer that includes determining a sensitivity for reporting defects detected on the wafer based on local attributes determined for different locations within a design for the wafer that do not have one or more of the disadvantages of currently used systems and methods.

SUMMARY OF THE INVENTION

The following description of various embodiments of methods, computer-readable media, and systems is not to be construed in any way as limiting the subject matter of the appended claims.

One embodiment relates to a computer-implemented method for generating an inspection process for a wafer. The method includes separately determining a value of a local attribute for different locations within a design for a wafer based on a defect that can cause at least one type of fault mechanism at the different locations. The method also includes determining a sensitivity with which defects will be reported for different locations on the wafer corresponding to the different locations within the design based on the value of the local attribute. In addition, the method includes generating an inspection process for the wafer based on the determined sensitivity.

In one embodiment, the value of the local attribute is critical radius of the defect that can cause at least one type of fault mechanism at the different locations. In another embodiment, the value of the local attribute is determined as a function of at least one dimension of one or more features of the design at the different locations, one or more features of the design proximate to the different locations, or some combination thereof. In a further embodiment, separately determining the value of the local attribute is performed using design data for the design. In an additional embodiment, the different locations span an entirety of the design. In some embodiments, separately determining the value of the local attribute is performed based on the defect that can cause the at least one type of fault mechanism at the different locations and one or more parameters of an inspection system that will perform the inspection process.

In one embodiment, the value of the local attribute has an inverse relationship to the sensitivity. In another embodiment, the determined sensitivity is different than a sensitivity with which defects will be detected at the different locations on the wafer. In an additional embodiment, the sensitivity is the sensitivity with which defects will be detected at the different locations on the wafer and reported for the different locations on the wafer. In a further embodiment, the sensitivity is a sensitivity to magnitude of a characteristic of individual output in output generated for the wafer during the inspection process.

In one embodiment, the method includes generating a map of the values of the local attribute as a function of the different locations within the design, and determining the sensitivity is performed using the map. In another embodiment, determining the sensitivity includes generating a map of the sensitivities with which the defects will be reported for the different locations on the wafer as a function of the different locations within the design.

In one embodiment, determining the sensitivity includes assigning the different locations within the design to different groups based on the value of the local attribute thereby assigning the different locations on the wafer corresponding to the different locations within the design that will have at least similar noise statistics to the same group. In another embodiment, determining the sensitivity includes assigning the different locations within the design to different segments based on the value of the local attribute and separately estimating noise statistics for the different segments. In one such embodiment, the noise statistics are noise statistics for output that would be generated during the inspection process at the different locations on the wafer corresponding to the different locations within the design assigned to the different segments. In one such embodiment, determining the sensitivity also includes determining the sensitivity for the different segments based on the noise statistics.

In one embodiment, determining the sensitivity includes assigning different portions of an entire range of values of the local attribute to different segments and separately determining different sensitivities for the different segments based on the values of the local attribute in the different portions assigned to the different segments. In one such embodiment, determining the sensitivity also includes separately assigning the different locations within the design to the different segments based on the different portions in which the values of the local attribute determined for the different locations fall. In another such embodiment, determining the sensitivity includes generating a map of the sensitivities with which defects will be reported for the different locations on the wafer as a function of the different locations within the design based on the value of the local attribute for the different locations, the different portions of the entire range of the values of the local attribute assigned to the different segments, and the different sensitivities determined for the different segments.

In one embodiment, the method includes separately determining a value of a local image attribute for the different locations on the wafer based on output generated for the wafer by an inspection system during the inspection process. In one such embodiment, determining the sensitivity is performed based on the values of the local attribute and the local image attribute. In another such embodiment, determining the sensitivity is performed based on the value of the local attribute, the value of the local image attribute, and coordinate inaccuracy of the inspection system.

In one embodiment, determining the sensitivity is performed based on the value of the local attribute and information about hot spots in the design. In another embodiment, the value of the local attribute does not indicate if the different locations within the design are hot spots in the design, and determining the sensitivity is not performed based on information about the hot spots in the design. In another embodiment, the design printed on the wafer cannot be resolved by an inspection system that performs the inspection process.

In some embodiments, separately determining the value of the local attribute and determining the sensitivity are performed before defects are detected on the wafer in the inspection process. In another embodiment, separately determining the value of the local attribute and determining the sensitivity are performed offline.

In one embodiment, using the inspection process, defects are detected based on magnitude of a characteristic of individual output in output generated for the wafer during the inspection process and are not detected based on size of the defects. In another embodiment, using the inspection process, the defects are reported based on magnitude of a characteristic of individual output in output generated for the wafer during the inspection process and are not reported based on size of the defects. In an additional embodiment, the inspection process includes determining a position of output generated for the wafer by the inspection system during the inspection process in design data space such that the output generated at the different locations on the wafer corresponding to the different locations within the design can be identified.

Each of the steps of each of the embodiments of the computer-implemented method described above may be further performed as described herein. In addition, each of the embodiments of the computer-implemented method described above may include any other step(s) of any other method(s) described herein. Furthermore, each of the embodiments of the computer-implemented method described above may be performed by any of the systems described herein.

Another embodiment relates to a computer-readable medium that includes program instructions executable on a computer system for performing a computer-implemented method for generating an inspection process for a wafer. The method includes separately determining a value of a local attribute for different locations within a design for a wafer based on a defect that can cause at least one type of fault mechanism at the different locations. The method also includes determining a sensitivity with which defects will be reported for different locations on the wafer corresponding to the different locations within the design based on the value of the local attribute. In addition, the method includes generating an inspection process for the wafer based on the determined sensitivity.

The computer-readable medium described above may be further configured according to any of the embodiment(s) described herein. Each of the steps of the computer-implemented method executable by the program instructions may be further performed as described herein. In addition, the computer-implemented method executable by the program instructions may include any other step(s) of any other method(s) described herein.

An additional embodiment relates to a system configured to generate and perform an inspection process on a wafer. The system includes a computer subsystem configured to separately determine a value of a local attribute for different locations within a design for a wafer based on a defect that can cause at least one type of fault mechanism at the different locations. The computer subsystem is also configured to determine a sensitivity with which defects will be reported for different locations on the wafer corresponding to the different locations within the design based on the value of the local attribute. In addition, the computer subsystem is configured to generate an inspection process for the wafer based on the determined sensitivity. The system also includes an inspection subsystem configured to perform the inspection process on the wafer.

The embodiment of the system described above may be further configured according to any of the embodiment(s) described herein. In addition, the embodiment of the system described above may be configured to perform any step(s) of any method embodiment(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
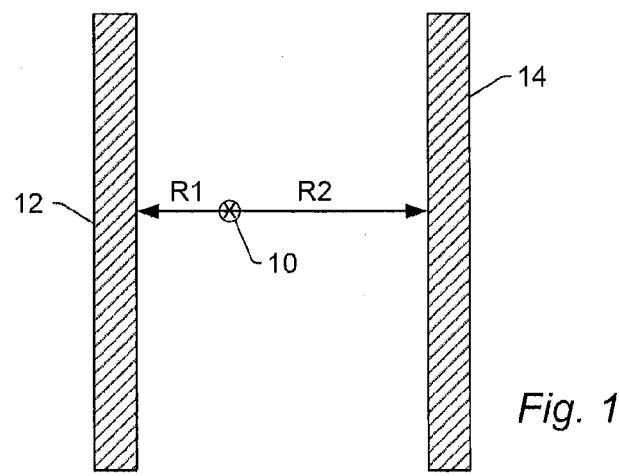
FIG. 1 is a schematic diagram illustrating a plan view of an example of how a critical radius of a defect, which can cause at least one type of fault mechanism at a location within a design for a wafer, can be determined.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits (ICs) may be formed on a wafer, and the term wafer as used herein is intended to encompass a wafer on which any type of device known in the art is being fabricated.

Although embodiments are described herein with respect to wafers, it is to be understood that the embodiments may be used for another specimen such as a reticle, which may also be commonly referred to as a mask or a photomask. Many different types of reticles are known in the art, and the terms "reticle," "mask," and "photomask" as used herein are intended to encompass all types of reticles known in the art.

The term "design" as used herein generally refers to the physical design (layout) of an IC and data derived from the physical design through complex simulation or simple geometric and Boolean operations. The design may include not only layout information, but electrical and material design information as well. Basically, the design may include any design information that is used in the creation of a "device." In addition, an image of a reticle acquired by a reticle inspection system and/or derivatives thereof can be used as a "proxy" or "proxies" for the design. Such a reticle image or a derivative thereof can serve as a substitute for the design in any embodiments described herein that use a design. The design may include any other design data or design data proxies described in commonly owned U.S. patent application Ser. Nos. 11/561,735 by Kulkarni et al., published as U.S. Patent Application Publication No. 2007/0156379 on Jul. 5, 2007, and 11/561,659 by Zafar et al., published as U.S. Patent Application Publication No. 2007/0288219 on Dec. 13, 2007, both of which were filed on Nov. 20, 2006 and both of which are incorporated by reference as if fully set forth herein.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for generating an inspection process for a wafer. The inspection process may be a number of different types of inspection processes. For example, the inspection process may be a bright field (BF) inspection process. In another example, the inspection process may be a dark field (DF) inspection process. The inspection process may also include performing only one type of inspection or different types of inspection on the wafer in the same scan or in multiple scans of the wafer. For example, the inspection process may include performing both DF and BF inspection of the wafer. Furthermore, the inspection process may include performing any other type of inspection known in the art, possibly in combination with the inspection types described above.

The method includes separately determining a value of a local attribute for different locations within a design for a wafer based on a defect that can cause at least one type of fault mechanism at the different locations. The different locations within the design may be defined in a number of different manners. For example, the different locations can be defined in an arbitrary or predetermined manner and may have any suitable dimensions. Each of the different locations may also have the same dimensions. The dimensions of the different locations may be selected such that the value of the local attribute is determined with relatively high resolution or with relatively low resolution across the design. The resolution with which the different locations are defined may vary depending on, for example, the resolution or pixel size of the inspection system that will be used to perform the inspection process. For example, the resolution with which the value of the local attribute is determined across the design may correspond to the resolution with which the output will be generated by the inspection system across the design printed on the wafer. The different locations may also be defined within the design such that the different locations span an entirety of the design.

The local attribute is "local" in that it is based on at least one type of fault mechanism at the different locations. In other words, the local attribute is determined based on information or attributes for less than the entire design but is determined based on information or attributes for a portion of the entire design that is greater than just each location, and that portion may vary depending on the design itself and the at least one fault mechanism. For example, if the fault mechanism is a short, then the information or attributes for the design that is or are used to determine the value of the local attribute for a location within the design may include information or attributes for features in the design that may be shorted if a defect is located at that location. Therefore, determining the value of the local attribute for a location in the design may be performed using attributes for, or information about, a "neighborhood" within the design surrounding the location, which may include attributes or information about the design at other different locations within the design. However, each value of the local attribute that is determined is determined for only one different location in the design. For example, a value of the local attribute is not determined for one location and then assigned to a number of other different locations. In addition, a value of the local attribute is not determined collectively for a number of different locations. Furthermore, even if the at least one fault mechanism on which the value of the local attribute is based may cause a global failure (e.g., complete failure of the device corresponding to the design), the value of the local attribute is still determined based on only local attributes or local information about the design. Although a short is used above as an example of a type of fault mechanism on which the value of the local attribute can be based, the at least one type of fault mechanism may include any other type of fault mechanism (e.g., open, etc.) known in the art. Moreover, the value of the local attribute may be determined based on different fault mechanisms at different locations in the design (e.g., depending on which type(s) of fault mechanisms a design is susceptible to at any given location, which can be determined in any suitable manner).

In one embodiment, the value of the local attribute is critical radius of the defect that can cause at least one type of fault mechanism at the different locations. In another embodiment, separately determining the value of the local attribute is performed using design data for the design. For example, separately determining the value of the local attribute may include extracting local critical attributes such as critical radius and/or local design information from design data (e.g., a graphical data stream (GDS)) for the design. Local design information can be generally defined as design information from the neighborhood of an inspection location. For example, critical radius is a local design attribute that may be used in the embodiments described herein. Polygon density is another local design attribute that may be used in the embodiments described herein. The design data for the design may be acquired from any suitable source such as a customer. In addition, the value of the local attribute may not be determined based on any output or information about or attributes for any output that is responsive to light from the wafer. For example, the value of the local attribute may be determined based on the design itself and information about defects that can cause at least one type of fault mechanism in the design but not based on information about how the design will affect light detected by the inspection system during the inspection process. Furthermore, the value of the local attribute may be determined as described herein and not based on the criticality of the features in the design to the functioning of the device. For example, even though the value of the local attribute is determined based on at least one type of fault mechanism that a defect at a location may cause, the value of the local attribute is not based on criticality of the features that will or can be affected by that at least one type of fault mechanism.

Critical radius r(x, y) is the minimum defect radius for different types of fault mechanisms such as opens and shorts that would occur if the center of the defect were to fall on (x, y). For example, as shown in FIG. 1, if a defect is located at location 10 between two patterned features 12 and 14 formed on a wafer, the center of the defect is located a distance R1 from patterned feature 12 and a distance R2 from patterned feature 14. As such, the defect will cause a short if the radius of the defect is equal to or greater than R2. Therefore, the critical radius of a defect located at location 10 is R2 ($r_{short}$(x, y)=R2). Critical radius was introduced by Wagner et al., "An interactive VLSI CAD tool for yield estimation," IEEE Transactions on Semiconductor Manufacturing, (1995) as a means to compute critical area. For a given defect having a radius r, critical area A(r) can be determined using the following equation: $A(r)=\{(x,y): r(x,y) \leq r\}$. Critical area can be determined in the embodiments described herein using this equation. Another algorithm that can be used to determine critical radius is described in commonly owned U.S. Pat. No. 6,918,101 to Satya et al., which is incorporated by reference as if fully set forth herein. Critical radius can be determined in the embodiments described herein as described in this patent.

Critical area analysis (CAA) may also be performed in a number of other ways. For example, critical area information may be determined in the embodiments described herein as described in commonly owned U.S. Pat. No. 6,813,572 to Satya et al., which is incorporated by reference as if fully set forth herein. Critical area information may also be determined for semiconductor design data as described in commonly owned U.S. Pat. Nos. 6,751,519 to Satya et al. and 6,948,141 to Satya et al., which are incorporated by reference as if fully set forth herein. The embodiments described herein may include any step(s) described in these patents.

Figure 2:
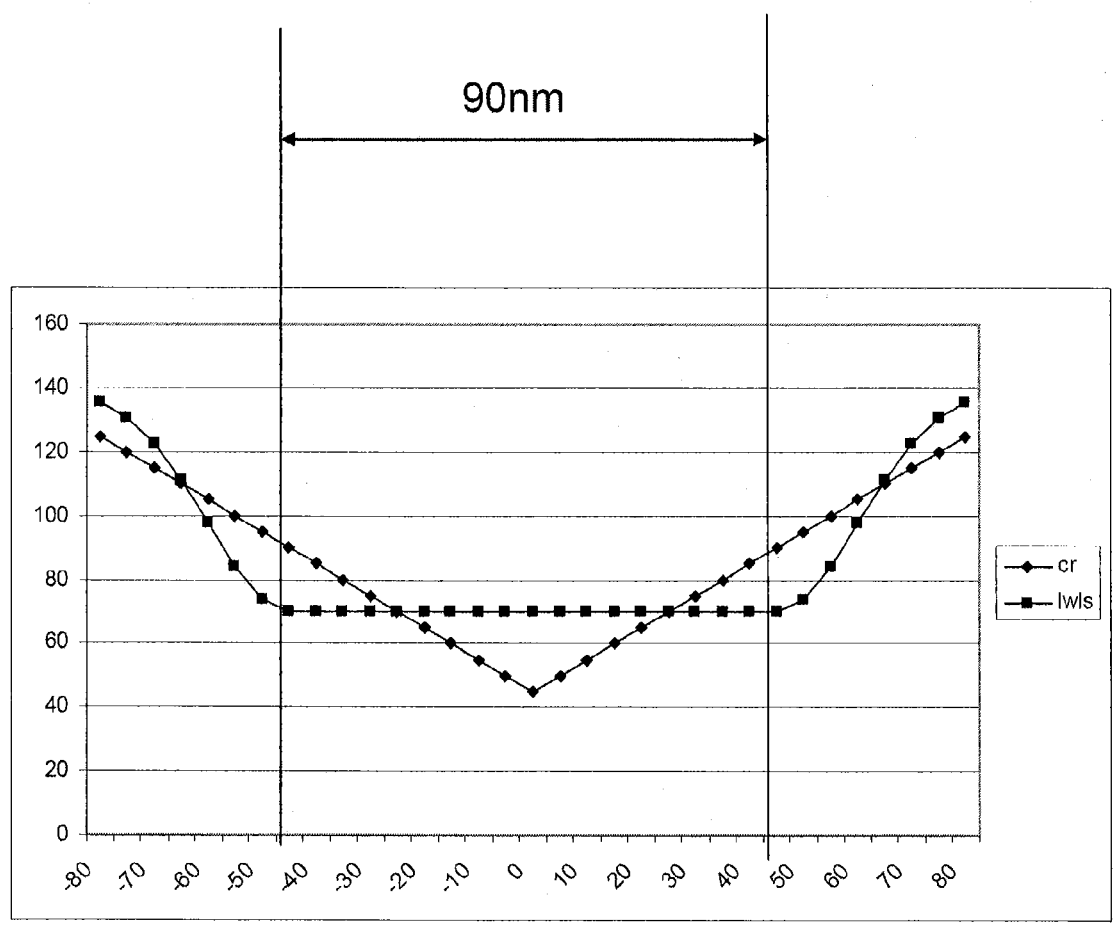
FIG. 2 is a plot showing values of different local attributes as a function of distance from the center of a feature in a design for a wafer.

In another embodiment, the value of the local attribute is determined as a function of at least one dimension of one or more features of the design at the different locations, one or more features of the design proximate to the different locations, or some combination thereof. For example, critical radius is just one local design attribute that can be used as described herein to determine the sensitivity. As described above, critical radius may be a function of at least one dimension of one or more features (e.g., line width and line space) in the design. Other functions of at least one dimension of one or more features in the design (e.g., line width and line space) can also be used to determine the sensitivity as described further herein. For example, as shown in FIG. 2, for a feature such as a line or a space having a width of 90 nm, the chart shows values of the critical radius (cr) in nm as a function of distance in nm from the center of the feature. In addition, FIG. 2 shows values of another function of line width and line space (lwls) in nm as a function of distance in nm from the center of the feature. In particular, the center of the feature is located at 0 nm in the plot. Therefore, since the feature has a width of 90 nm, the feature extends from −45 nm to 45 nm on the x axis of the plot. As further shown in FIG. 2, the values of critical radius have one function from the center of the feature, while the values of line width and line space have a different function from the center of the feature. For example, the critical radius may have one function of line width or line space. The critical radius may be determined as described herein. However, the value of the local attribute can also be defined by another function of the line width or line space. In addition, height information of the features in the third dimension in the space can be used to extract the local design attribute. The values of any such different local attributes may be used as described herein.

The one or more features of the design proximate to any one of the different locations, at least one dimension of which is used to determine the local attribute, may include one or more features that are located some distance away from the location, and in that sense are not adjacent to the location. However, the one or more features may be proximate to the different location in that there are no other features located between the one or more features and the location. In addition, the one or more features, at least one dimension of which is used to determine the local attribute, may be located different distances from the location.

In some embodiments, separately determining the value of the local attribute is performed based on the defect that can cause the at least one type of fault mechanism at the different locations and one or more parameters of an inspection system that will perform the inspection process. For example, local design information such as any of the local design information described further herein may be combined with inspection system parameter(s) (e.g., image settings such as light angle) to determine the value of the local attribute.

In some embodiments, the different locations span an entirety of the design. For example, separately determining the value of the local attribute may include extracting local critical or design attributes such as critical radius from design data (e.g., GDS) for the design at each pixel. In this manner, each of the different locations may be defined as a pixel in the design. The pixels in the design may correspond to the pixels in inspection. In this manner, the local critical or design attributes may be extracted for each pixel in inspection. However, each pixel in the design may be smaller than the inspection pixel size because it is extracted from the design data. As such, the value of the local attribute can be separately determined at different locations across the entire design. Determining the value of the local attribute across the entire design may be advantageous particularly if the entire design printed on the wafer (or the entire area of the design on the wafer) will be inspected in the inspection process. However, if the inspection process will involve inspecting only a portion of the design printed on the wafer or only a portion of the entire area of the design on the wafer (e.g., if the coverage mode of the inspection process is less than 100% of the die area), the value of the local attribute may be separately determined for only that portion of the design or only that portion of the entire area of the design that will be inspected.

The local attributes described above can be used in inspection in a number of different manners described further herein. For example, the method includes determining a sensitivity with which defects will be reported for different locations on the wafer corresponding to the different locations within the design based on the value of the local attribute. In this manner, the embodiments described herein determine sensitivity using local design information. For example, the embodiments described herein utilize design based criticality analysis, which has traditionally been a part of yield prediction, in determining inspection sensitivity. In this manner, the embodiments described herein can use design based information to connect yield with inspection sensitivity. For example, the values of the local attribute such as critical radius and other critical attributes described above, which are related to yield, that may be determined as described herein can be used to determine inspection sensitivity. In this manner, the embodiments described herein can use critical radius and other critical attributes or other design based critical attributes to determine inspection sensitivity. Since at least some of the different locations within the design for the wafer will have different values of the local attribute, the sensitivity that is determined for at least some of the different locations will be different. As such, the sensitivity that is used for at least some of the different locations in the design and corresponding locations on the wafer will be different.

The embodiments described herein, therefore, may use critical radius and/or other local attributes described herein in a novel way, which is to determine inspection sensitivity, while critical radius and other local attributes have traditionally been used for critical area analysis and yield prediction. As such, the embodiments described herein essentially introduce design based criticality analysis into defect detection. The term "using design based criticality analysis to determine inspection sensitivity" is used interchangeably herein with the terms "using critical radius and other critical attributes for defect detection" and "design based sensitivity map." The embodiments described herein can be used to enhance inspection sensitivity as will be described further herein. In particular, the embodiments use design based critical attributes to enhance inspection sensitivity.

In one embodiment, the value of the local attribute has an inverse relationship to the sensitivity. For example, if the value of the local attribute is critical radius, as the critical radius decreases, the sensitivity should be increased. In addition, as described further herein, the method may include generating a map of the values of the local attribute. In this manner, for a relationship between the value of the local attribute and the sensitivity described above, for pixels in the map that have lower values, the higher the sensitivity should be at the pixels. However, the value of the local attribute may have other relationships to the sensitivity. For example, if the value of the local attribute is polygon density, as the polygon density increases, the sensitivity should be increased. Therefore, the value of the local attribute may not have an inverse relationship to the sensitivity.

The manner in which the sensitivity is determined may vary depending on the local attribute for which values are determined at different locations in the design. For example, if the local attribute is critical radius, the sensitivity may be determined to be a value just below the critical radius or a value that corresponds to the critical radius. In another example, if the local attribute is critical radius, the sensitivity for the smallest determined values of the critical radius may be determined as the highest possible sensitivity and the sensitivity for the largest determined values of the critical radius may be determined to be the lowest possible sensitivity. The sensitivity for determined values of the critical radius that are between the smallest and the largest values may be determined to be a sensitivity between the highest possible sensitivity and the lowest possible sensitivity. In addition, the manner in which the sensitivity is determined may vary depending on the defect detection algorithm and/or method that will be used in the inspection process. For example, if the defect detection algorithm and/or method has a "continuously variable" sensitivity or does not use segments, each different value of the local attribute can be associated with a different sensitivity. In such instances, the value of the local attribute and the sensitivity may have an inverse, and possibly also linear, relationship. However, if the defect detection algorithm and/or method uses segments, which can be associated with different sensitivities, different ranges of values of the local attribute can be associated with a segment (as described further herein) and therefore with the sensitivity associated with that segment or a sensitivity can be collectively determined for the different values of the local attribute associated with one segment.

In one embodiment, the determined sensitivity is different than a sensitivity with which defects will be detected at the different locations on the wafer. For example, as described herein, the determined sensitivity is the sensitivity with which defects will be reported, which may not be the same as the sensitivity with which defects will be detected. As such, the determined sensitivity may be an inspection sensitivity. In this manner, the inspection sensitivity may not be the same as the detection sensitivity. For example, the defects can be detected with one sensitivity and then reported at another sensitivity (e.g., by filtering the detected defects based on some criteria to thereby arrive at the reported defects).

In an additional embodiment, the sensitivity is the sensitivity with which defects will be detected at the different locations on the wafer and reported for the different locations on the wafer. In addition, as described above, the local attribute may be critical radius. In this manner, the embodiments described herein may use critical radius in a novel way (e.g., to determine detection sensitivity). However, any of the local design attributes described herein can be used in defect detection to determine the detection sensitivity based on the criticality of patterns in the design. As such, the sensitivity with which defects are detected may be the same as the sensitivity with which defects are reported. In this manner, all of the defects that are detected may also be reported. Therefore, the defects that are detected may not be filtered prior to being reported.

Regardless of the sensitivity that is determined as described herein, the defects may be reported in any suitable manner. For example, the defects may be reported by performing the inspection process on the wafer, generating results of the inspection process, and storing the results such that the results can be displayed to a user, used in the method and/or system embodiments described herein, used by another method and/or system, and the like. The results of the inspection process may have any suitable format (e.g., a KLARF file) and may be stored in any suitable storage medium including any of those described herein. In addition, the inspection results may include any suitable information about the defects detected on the wafer.

In another embodiment, the sensitivity is a sensitivity to magnitude of a characteristic of individual output in output generated for the wafer during the inspection process. For example, the magnitude of the characteristic of the individual output may be a magnitude of intensity of individual output corresponding to a defect or "defect magnitude." Defect magnitude is different than defect size in that defect magnitude refers to the gray level of the individual output corresponding to a defect while defect size generally refers to the number of pixels of the individual output that are determined to correspond to the defect. In this manner, the defect magnitude corresponds to how "strong" the defect is or how strongly the defect reflects or scatters light that is detected by the inspection system. In some instances, the defect magnitude may be an absolute value of the difference between the defect image and a reference image. Therefore, the defect magnitude may be determined using a number of different currently used defect detection algorithms. For example, a defect detection algorithm that performs a die-to-die comparison of output generated for a wafer and then thresholds the results of the comparison to detect defects on the wafer can be used to determine the defect magnitude (e.g., the results of the die-to-die comparison). Therefore, the embodiments described herein may build a connection between design based criticality analysis and defect magnitude in inspection. In addition, as described above, the local attribute may be critical radius. As such, the embodiments described herein may combine critical radius with defect magnitude. In other words, critical radius can be combined with defect magnitude because the critical radius can essentially be used in defect detection as described herein, and defect detection can be performed by thresholding defect magnitude. However, any of the other local attributes described herein can also be combined with defect magnitude in a similar manner. In this manner, the embodiments described herein may not rely on or use defect size information.

When defects are relatively or substantially small, the embodiments described herein may be particularly advantageous because it may not be defect sizes that matter but defect magnitude. For example, defect size reported by an inspection system may not be reliable due to limitations of the imaging subsystem of the inspection system (e.g., limitations of resolution and/or pixilation) and limitations of the inspection algorithm. Therefore, the "real" defect size (e.g., determined by scanning electron microscope (SEM) review) may be substantially different from the defect size determined by inspection (e.g., BF inspection). Defect size is especially not reliable for substantially small defects. For example, a difference in defect size from 1 pixel to 2 pixels may be only due to pixelization, not any difference in actual defect size. On the other hand, defect magnitude or energy for substantially small defects could be more reliable.

In some embodiments, the method includes generating a map of the values of the local attribute as a function of the different locations within the design. For example, the method may include generating a map of critical radius values or any other local attribute values as a function of the different locations within the design. In some such examples, different gray levels in the map may correspond to different values of the critical radius or other local attribute. For example, each gray level may correspond to 1 nm of critical radius. In other words, each gray level increment may corresponding to a 1 nm increment in critical radius. Therefore, the map may be a gray level image having a resolution that is defined by the dimensions of the different locations relative to the dimensions of the design. However, the map may have any suitable format such as a two-dimensional (2D) plot showing the values of the local attribute as a function of the different locations or a three-dimensional (3D) plot of the values of the local attribute as a function of the different locations.

In the example in which the local attribute is critical radius, the method may to include creating a critical radius map prior to inspection of the wafer from design data for the wafer. The critical radius map is a critical area map in which each value in the critical area map is the radius of a defect that can cause a fault in the design. In particular, the critical radius map may include the minimum defect size that can cause a fault such as a short or open at different locations in the map. For example, in a real time implementation of the method, the design data can be pre-processed to create a critical radius map, i.e., a 3D version of a critical area map in which each value in the map indicates the radius of the defect size that can cause a fault in the design. In this manner, the embodiments described herein are advantageous in that the method may include pre-processing the design to create the critical radius map. Creating the critical radius map from the design data may be performed using any suitable method or system. For example, one efficient method for creating a critical radius map is described in commonly owned U.S. Pat. No. 6,918,101 to Satya et al., which is incorporated by reference as if fully set forth herein. The embodiments described herein may include any step(s) of any method(s) described in this patent. In addition, a map of any other local attribute values described herein may be generated in a similar manner (e.g., by pre-processing design data for the wafer prior to inspection of the wafer).

The map of the values of the local attribute may not include the design data for the wafer. In this manner, the generated map may not contain the original design for the wafer. Therefore, if an inspection process is generated as described further herein such that the inspection process uses the map, a recipe for the inspection process that includes or uses such a map can be portable without any intellectual property issues related to sharing of the device design.

In one such embodiment, determining the sensitivity is performed using the map. For example, since the map includes the values of the local attribute for the different locations within the design, the map may be used to determine the sensitivity as described herein for the different locations on the wafer corresponding to the different locations within the design.

In one embodiment, determining the sensitivity includes generating a map of the sensitivities with which the defects will be reported for the different locations on the wafer as a function of the different locations within the design. In this manner, the embodiments described herein may include generating a design based sensitivity map based on or using local critical or design attributes such as critical radius or any other local attributes described herein. For example, the embodiments described herein may include utilizing design based criticality analysis in determining inspection sensitivity and generating a design based sensitivity map. As described above, the value of the local attribute may have an inverse relationship to the sensitivity. For example, the value of the sensitivity may essentially be the reverse of critical radius. In this manner, the sensitivity map may essentially be the reverse of the critical radius map. In addition, the gray levels in the sensitivity map may correspond to different sensitivity values. For example, each gray level may correspond to a sensitivity to 10 nm of defect size. In this manner, the higher value a map is at a pixel in the map, the higher the sensitivity should be at the pixel. However, as described herein, the sensitivity may have any relationship to the local attribute, and the relationship may vary depending on the local attribute. Furthermore, the sensitivity map can be defined by critical radius, which is one function of at least one dimension of one or more features of the design (e.g., line width or line space). In addition, the sensitivity map can be defined by another function of at least one dimension of one or more features of the design (e.g., line width or line space). In addition, although the map of sensitivities may be generated using the map of the values of the local attribute, the map of the sensitivities may be generated using the values of the local attribute having any format described herein.

The sensitivity map may be further configured as described herein. For example, the sensitivity map may be a gray level image having a resolution that is defined by the dimensions of the different locations relative to the dimensions of the design. However, the map may have any suitable format such as a 2D plot showing the values of the sensitivity as a function of the different locations or a 3D plot of the values of the sensitivity as a function of the different locations. In addition, the map of the values of the sensitivity may not include the design data. In this manner, the generated map may not contain the original design for the wafer. Therefore, if an inspection process is generated as described further herein such that the inspection process uses the map, a recipe for the inspection process that includes or uses such a map can be portable without any intellectual property issues related to sharing of the device design.

In one embodiment, determining the sensitivity includes assigning the different locations within the design to different groups based on the value of the local attribute thereby assigning the different locations on the wafer corresponding to the different locations within the design that will have at least similar noise statistics to the same group. For example, any of the local design attributes described herein can be used in defect detection to generate segments, regions, or groups of different locations in the design that have at least similar values of the local attribute. In addition, using the local design attributes described herein to group the different locations within the design tends to group pixels in the design with similar noise statistics together. Grouping the different locations in the design in this manner effectively groups corresponding locations on the wafer that will have at least similar noise statistics into the same group. Grouping pixels in this manner can be an important step performed by defect detection algorithms such as segmented auto-thresholding (SAT) algorithms and multiple die auto-thresholding (MDAT) algorithms. Assigning the different locations within the design to the different groups based on the value of the local attribute may be performed as described further herein. The noise statistics may include any of the noise statistics described herein.

In another embodiment, determining the sensitivity includes assigning the different locations within the design to different segments based on the value of the local attribute and separately estimating noise statistics for the different segments. Assigning the different locations within the design to different segments based on the value of the local attribute may be performed as described further herein. Estimating noise statistics for the different segments may be performed in any suitable manner. In one such embodiment, the noise statistics are noise statistics for output that would be generated during the inspection process at the different locations on the wafer corresponding to the different locations within the design assigned to the different segments. For example, the noise statistics may be simulated based on information about the design and information about one or more parameters of the inspection system that will be used in the inspection process. In one such example, output (e.g., signals) that would be produced at the corresponding different locations on the wafer may be simulated, and the simulated output for the different locations assigned to one segment may be used to estimate the noise statistics for that segment. The noise statistics may include any suitable statistics or statistics of interest. For example, the noise statistics may include mean noise, average noise, maximum noise, and the like. Alternatively, output that is generated for one or more wafers may be used to separately estimate the noise statistics for the different segments. For example, output produced at corresponding locations on the wafer (or a different wafer) assigned to one segment may be used collectively to determine noise statistics for that segment. The noise statistics may include any of the noise statistics described above. In this manner, any of the local design attributes described herein can be used in defect detection for better segmentation than that produced by other segmentation methods, which may lead to better noise statistics estimation for the different segments.

In one such embodiment, determining the sensitivity includes determining the sensitivity for the different segments based on the noise statistics. For example, any of the local design attributes described herein can be used in defect detection for better segmentation than that produced by other segmentation methods, which may lead to better noise statistics estimation for the different segments. In addition, better segmentation or pixel grouping may lead to more reliable noise statistics for segments or groups and therefore enhanced sensitivity for the segments or groups. In particular, the sensitivity to be used for different segments can be determined based on the noise statistics. For example, the sensitivity or a parameter of a defect detection algorithm and/or method that is related to the sensitivity (e.g., a threshold) may be determined based on the noise statistics such that the defect detection algorithm and/or method detects a minimum amount of noise as potential defects. In one such example, if the noise statistics include average noise, a threshold for a segment may be set above the average noise to reduce the amount of noise that is detected as potential defects. Therefore, since the noise statistics are more reliable, the sensitivity determined for the different segments based on the noise statistics will be improved compared to other methods for determining sensitivity based on noise statistics.

In another embodiment, determining the sensitivity includes assigning different portions of an entire range of values of the local attribute to different segments and separately determining different sensitivities for the different segments based on the values of the local attribute in the different portions assigned to the different segments. In this manner, segmentation may associate each value of the local attribute to different sensitivity levels. For example, assigning different portions of an entire range of values of the local attribute to different segments may include histogram based thresholding. In particular, assigning different portions of an entire range of values of the local attribute to different segments may include generating a histogram of the values of the local attribute that are determined for the different locations and then determining the segments based on that histogram (e.g., using thresholding). However, determining the segments may not include generating or using a histogram. For example, if the values of the local attribute are critical radius, a user may want all pixels with a critical radius of less than about 45 nm to be very hot (i.e., assigned to a segment that is associated with "hot" defect detection parameters such as a "hot" threshold), all pixels with a critical radius of greater than 200 nm to be very cold (i.e., assigned to a segment that is associated with "cold" defect detection parameters such as a "cold" threshold), and all other pixels to be medium (i.e., assigned to a segment that is associated with defect detection parameters between "hot" and "cold"). Different sensitivities can then be assigned to the different segments as described herein. For example, the sensitivity assigned to a segment may be determined based on the criticality of the segment, the values of the local attribute associated with the segment, or user-selected parameters described above. In particular, the more critical a segment is, the more sensitive the inspection process should be for the segment. Furthermore, the design based sensitivity map can be used without segmentation.

In one embodiment, the method includes separately assigning the different locations within the design to the different segments based on the different portions in which the values of the local attribute determined for the different locations fall. For example, once the portions of the entire range of values of the local attribute are assigned to the different segments, each value of the local attribute that is determined for a different location can be compared to those portions. The segment corresponding to the portion in which a value falls is then determined as the segment to which the different location for which that value has been determined is to be assigned. In this manner, the different locations can be assigned to different segments. In addition, any other manner of assigning the different locations to segments may be used in the embodiments described herein.

In another embodiment, the method includes generating a map of the sensitivities with which defects will be reported for the different locations on the wafer as a function of the different locations within the design based on the value of the local attribute for the different locations, the different portions of the entire range of the values of the local attribute assigned to the different segments, and the different sensitivities determined for the different segments. In this manner, the method may include generating a segmented design based sensitivity map, and the segmentation then associates each pixel to different sensitivity levels. For example, the segmented design based sensitivity map may include different values for different segments such that the different segments (e.g., a hot segment and a cold segment) can be visually identified in the map. In other words, once a location is assigned to a segment, which may be performed as described herein, the sensitivity associated with that segment may be shown in a map at that location. As such, only the sensitivities that are assigned to segments will be shown in the map thereby creating a segmented design based sensitivity map. The segmented design based sensitivity map may be further configured as described herein.

In one embodiment, the method includes separately determining a value of a local image attribute for the different locations on the wafer based on output generated for the wafer by an inspection system during the inspection process. For example, mean and/or range of intensity, noise floor, or some combination thereof has been used to determine inspection sensitivity. In particular, some defect detection algorithms are configured to determine mean and/or range of intensity and noise floor of output generated during an inspection process and to determine the inspection sensitivity that is to be used for that output based on the mean and/or range and noise floor. Examples of such algorithms include the auto-thresholding (AT), SAT, and MDAT algorithms, which are used by commercially available inspection systems from KLA-Tencor, San Jose, Calif. Therefore, any of those algorithms can be used to separately determine a value of a local image attribute for different locations on the wafer in the embodiments described herein.

However, unlike currently used inspection processes that use such algorithms, in the embodiments described herein the value of the local image attribute is not used alone to determine inspection sensitivity. For example, in one embodiment, determining the sensitivity is performed based on the values of the local attribute and the local image attribute. In one such example, the method may include combining design based local critical attributes and local image attributes (such as mean and/or range) or other information from the image to determine the sensitivity of the detection algorithm at each pixel. Some currently used defect detection algorithms define segments based on image mean and range. However, in contrast to those defect detection algorithms, the embodiments described herein essentially bring a new dimension into the sensitivity segment determination (e.g., the design based sensitivity map). In this manner, the criticality information can be used together with the currently used local image attributes/information to determine inspection sensitivity. For example, once the sensitivity is determined based on the values of the local attribute for the different locations within the design, the sensitivity can be adjusted based on attributes or information about the image acquired at the corresponding locations on the wafer. For instance, if the image acquired on the wafer at a location is relatively noisy, the sensitivity assigned to the corresponding location within the design based on the value of the local attribute can be decreased to reduce the number of false defects or noise or nuisance events that are detected at that location due to the noise. In contrast, if the image acquired on the wafer at a location is relatively quiet, the sensitivity assigned to the corresponding location within the design based on the value of the local attribute can be increased such that defects can be detected at that location with greater sensitivity.

In another embodiment, determining the sensitivity is performed based on the value of the local attribute, the value of the local image attribute, and coordinate inaccuracy of the inspection system. For example, the method may include combining design based local critical attributes and local image attributes (such as mean and/or range) or other information from the image to determine the sensitivity of the detection algorithm at each pixel as described above with the consideration of coordinate inaccuracy. In one such example, if the coordinate inaccuracy is about 1 pixel and if the local attribute is critical radius, the minimum critical radius within a 3 pixel by 3 pixel neighborhood around any one pixel in the design and the local image attributes within a 3 pixel by 3 pixel neighborhood around the corresponding pixel in the output generated for the wafer by the inspection system may be used to determine the sensitivity for that one pixel. In this manner, the probability that the sensitivity that is used for each pixel is different than it should be can be reduced.

In one embodiment, determining the sensitivity is performed based on the value of the local attribute and information about hot spots in the design. For example, the methods described herein can combine hot spot information from a customer and local design attributes determined directly from design data (e.g., GDS) to determine inspection sensitivity. In particular, a semiconductor device design is verified by different procedures before production of ICs. For example, the semiconductor device design may be checked by software simulation to verify that all features will be printed correctly after lithography in manufacturing. Such checking commonly includes steps such as design rule checking (DRC), optical rule checking (ORC), and more sophisticated software based verification approaches that include process simulation calibrated to a specific fab and process. The output of the physical design verification steps can be used to identify a potentially large number of critical points, sometimes referred to as "hot spots," in the design. A "hot spot" may be generally defined as a location in the design data printed on the wafer at which a killer defect may be present. Therefore, the hot spots are often discovered by the creator of the design, who is often the customer of inspection system manufacturers or the customer of an inspection system user.

The hot spot information combined with the local design attributes may be used in any manner to determine the inspection sensitivity. For example, the methods described herein may use the hot spot information from a customer and local design attributes determined directly from GDS to generate a sensitivity map. In addition, the sensitivity may be determined in any manner as described herein based on the values of the local attribute, and then the determined sensitivity can be adjusted based on the information about the hot spots in the design. For example, if a particular location in the design is determined based on the hot spot information to be a location of a hot spot in the design, the sensitivity determined for that location can be evaluated to determine if the sensitivity can or should be increased. In contrast, if a particular location in the design is determined based on the hot spot information to not be a location of a hot spot in the design, the sensitivity determined for that location can be evaluated to determine if the sensitivity can or should be decreased.

In some embodiments, the value of the local attribute does not indicate if the different locations within the design are hot spots in the design, and determining the sensitivity is not performed based on information about the hot spots in the design. For example, if hot spots are to be used for inspection and/or determining sensitivity, information about the hot spots must often be acquired from the customer. However, as described further herein, the value of the local attribute may be determined directly from the design (and a defect that can cause at least one type of fault mechanism at the different locations). In addition, the sensitivity is determined based on the value of the local attribute. Therefore, these steps may not be performed based on, and therefore may not require, information about hot spots. Furthermore, none of the steps of any of the method embodiments described herein may be performed based on, and therefore may not require, information about hot spots.

In one embodiment, the design printed on the wafer cannot be resolved by an inspection system that performs the inspection process. For example, when design rules shrink, many patterns cannot be resolved by inspection systems. In this manner, image based attributes and/or information may not be sufficient to determine the sensitivity. However, the embodiments described herein use design based critical attributes to enhance inspection sensitivity and therefore do not need to rely on any image based attributes and/or information to determine the sensitivity. For example, the design based sensitivity map can be used without combining local image attributes with the map. In addition, image based attributes or information such as mean and range may not be sufficient to differentiate segments. However, the embodiments described herein can use the values of the local attribute for different locations within a design to differentiate the segments and therefore do not need to rely on any image based attributes or information to differentiate the segments. However, as further described herein, image based attributes and/or information can be used in combination with the values of the local attribute for different locations within a design to determine the sensitivity.

In another embodiment, separately determining the value of the local attribute and determining the sensitivity are performed before defects are detected on the wafer in the inspection process. For example, the embodiments described herein can be performed in the detection part of an inspection process. In this manner, some step(s) of the method may be performed during the inspection process or in-situ. For example, some step(s) of the method may be performed during scanning of the wafer using an existing inspection process, and then the results of the step(s) may be used to alter one or more parameters (e.g., the sensitivity) of the existing inspection process thereby effectively generating an inspection process.

In an additional embodiment, separately determining the value of the local attribute and determining the sensitivity are performed offline. For example, the embodiments described herein, or at least some of the steps of the embodiments described herein, can be performed offline in pre-processing. In one such example, handling the GDS, determining critical radius, generating the sensitivity map, and storing the sensitivity map can be performed offline during pre-processing. Online processing may include determining the position of the output generated for the wafer during scanning in design data space and retrieving the sensitivity map in real time. Determining the position of the output in design data space may be performed as described in the above-referenced patent application by Kulkarni et al. In addition, online processing may include combining the design based sensitivity map and the image based sensitivity map. Furthermore, the embodiments described herein can be performed in post-processing of the inspection process.

The method further includes generating an inspection process for the wafer based on the determined sensitivity. Generating the inspection process may include storing a map of the sensitivities that may be generated as described herein and configuring an inspection process recipe such that the map is retrieved and used during the inspection process. In one embodiment, the inspection process includes determining a position of output generated for the wafer by the inspection system during the inspection process in design data space such that the output generated at the different locations on the wafer corresponding to the different locations within the design can be identified. For example, the inspection process may include determining the position of the output in design data space and assigning a sensitivity to the output based on the sensitivities assigned to the different locations within the design and the positions of the different locations in design data space. In addition, during the inspection process, the map may be retrieved and aligned to the output generated in the inspection process such that individual sensitivities in the map can be applied to the individual output aligned to the map. Since the map of sensitivities is generated as a function of the different locations in the design, aligning the map to the output essentially determines the position of the output in design data space. Therefore, aligning the map of the sensitivities to the output may be performed by determining a position of the output in design data space using a method and/or system such as those described in the above-referenced patent application by Kulkarni et al. In addition, aligning the map of the sensitivities to the output may be performed by using any method or system for aligning design data to a gray level image. The inspection process may also be generated such that the map of the sensitivities with which the defects will be reported for the different locations is stored and used by a defect detection algorithm used in the inspection process. For example, the map of the sensitivities could be used as a feature dimension in a defect detection algorithm such as the MDAT algorithm.

In one embodiment, using the inspection process, defects are detected on the wafer based on magnitude of a characteristic of individual output in output generated for the wafer during the inspection process and are not detected based on size of the defects. For example, as described above, the sensitivity may be a sensitivity to magnitude of a characteristic of individual output in output generated for the wafer during the inspection process, and the sensitivity may be a sensitivity with which the defects are detected. In addition, the magnitude of the characteristic of the individual output may be a magnitude of individual output corresponding to a defect or "defect magnitude." Therefore, since the detection sensitivity may be determined in terms of magnitude of the characteristic of the individual output, the defects may be detected in the inspection process in terms of magnitude instead of defect size. For example, the inspection process may be configured to use a defect detection algorithm that performs a die-to-die comparison to determine a magnitude of the intensity of the individual output, and a threshold, which may be determined based on the sensitivity determined by the embodiments described herein or which may be associated with the sensitivity determined by the embodiments described herein, may be applied to the results of the comparison to detect defects on the wafer thereby detecting defects on the wafer based on magnitude and not based on size.

In another embodiment, using the inspection process, the defects on the wafer are reported based on magnitude of a characteristic of individual output in output generated for the wafer during the inspection process and are not reported based on size of the defects. For example, as described above, the sensitivity may be a sensitivity to magnitude of a characteristic of individual output in output generated for the wafer during the inspection process, and the sensitivity may be a sensitivity with which the defects are reported. In addition, the magnitude of the characteristic of the individual output may be a magnitude of individual output corresponding to a defect or "defect magnitude." Therefore, since the sensitivity with which defects are reported may be determined in terms of magnitude of the characteristic of the individual output, the defects may be reported in the inspection process based on magnitude instead of defect size. For example, the inspection process may be configured to use a defect detection algorithm that performs a die-to-die comparison to determine a magnitude of the intensity of the individual output, and a threshold, which may be determined based on the sensitivity determined by the embodiments described herein or which may be associated with the sensitivity determined by the embodiments described herein, may be applied to the results of the comparison to detect defects on the wafer thereby detecting defects on the wafer based on magnitude and not based on size. If the sensitivity with which the defects are detected is the same as the sensitivity with which the defects are reported, the detected defects may be reported. For example, all of the detected defects may be reported. However, if the sensitivity with which the defects are detected is different than the sensitivity with which the defects are reported, the defects may be detected as described above or in any other manner, which may or may not be based on defect magnitude, and then the detected defects may be filtered based on defect magnitude to thereby produce the defects that are to be reported. In this manner, the defects may be reported based on defect magnitude instead of defect size.

The embodiments described herein may also include performing the generated inspection process on the wafer. The generated inspection process may be performed on the wafer in any suitable manner. In this manner, the embodiments described herein may include generating inspection results for the wafer by performing the generated inspection process on the wafer. The inspection results may include information about defects detected on the wafer during the inspection process and determined to be reported (i.e., determined to be included in the inspection results). The inspection results may have any suitable format described herein.

The embodiments described herein have a number of advantages over other methods and systems for generating an inspection process. For example, in the past, wafer inspection tools may only use images acquired from the wafer to determine sensitivity. However, due to the limitations of image resolution capability of inspection systems, the underlying circuit patterns are usually not resolved. It is not until recently that the industry began to look for ways to improve the inspection results by utilizing the design of the wafer.

One example of this trend is context based inspection (CBI). Examples of methods and systems for performing CBI are described in the above-referenced patent application by Kulkarni et al. In addition, examples of methods and systems for design based inspection are described in that application. The methods and systems described in this patent application can use many aspects of design information because a context map could be a number of different design information/attributes. In addition, the methods and systems described in this patent application relate to many aspects of inspection such as determining sensitivity, nuisance filtering, defect classification, and defect ranking or sampling. While the methods and systems described in this patent application relate to using context information to determine sensitivity in general, the methods and systems described in this patent application are not configured for performing at least some of the step(s) described herein (e.g., how to extract context information and using it to determine sensitivity as described herein).

Another example of a currently used method is hot spot based inspection. Hot spot based inspection basically uses hot spot information from customers in the inspection. However, hot spot based inspection is disadvantageous because it relies on hot spot information from customers. In contrast with hot spot based inspection, the embodiments described herein may not rely on hot spot information from customers. For example, the embodiments described herein determine sensitivity using local design information and may not rely on hot spot information from customers.

An additional example of a currently used method involves determining defect criticality index (DCI) for defects detected on wafers and is performed on "leaf" computers ("DCI on leaf"). DCI on leaf determines the DCI by using CAA for given defect sizes after defect detection. In this manner, DCI on leaf combines critical radius with defect size reported by inspection. DCI on leaf, therefore, relies on defect size information reported by inspection. But when defects are relatively or substantially small, it may not be defect sizes that matter, but defect magnitude. Furthermore, sometimes defect sizes reported by inspection are not accurate. Additional examples of methods and systems for determining DCI for defects on wafers are illustrated in commonly owned U.S. patent application Ser. No. 12/102,343 by Chen et al. filed Apr. 14, 2008, which is incorporated by reference as if fully set forth herein, and the above-referenced patent application by Zafar et al.

In contrast to DCI on leaf, therefore, the embodiments described herein combine critical radius or other local attribute with defect magnitude. In this manner, the embodiments described herein may not rely on defect size information reported by inspection. When defects are relatively or substantially small, the embodiments described herein may be advantageous because it may not be defect sizes which matter but defect magnitude. In addition, the ways in which the embodiments described herein may use critical radius or another local attribute are different than the ways in which DCI on leaf uses critical radius. For example, DCI on leaf uses critical radius in a traditional way (e.g., determining critical area (CA) for a given defect size). In contrast, the embodiments described herein may use critical radius or another local attribute in a novel way, to determine detection sensitivity. Furthermore, the embodiments described herein and DCI on leaf may be implemented in different parts of an algorithm. For example, DCI on leaf has to be performed after detection and in post-processing because it relies on defect size reported by inspection. In contrast, the embodiments described herein may be performed in the detection part, although they could be performed in post-processing as well.

Each of the embodiments of the method described above may include any other step(s) of any method(s) described herein. In addition, each of the embodiments of the method described above may be performed by any system embodiments described herein.

Any of the methods described herein may include storing results of one or more steps of one or more methods described herein in a storage medium. The results may include any of the results described herein. The results may be stored in any manner known in the art. In addition, the storage medium may include any storage medium described herein or any other suitable storage medium known in the art. After the results have been stored, the results can be accessed in the storage medium and used by any of the method or system embodiments described herein or any other method or system. Furthermore, the results may be stored "permanently," "semi-permanently," temporarily, or for some period of time. For example, the storage medium may be random access memory (RAM), and the results may not necessarily persist indefinitely in the storage medium. In addition, the results of any of the step(s) of any of the method(s) described herein can be stored using systems and methods such as those described in commonly owned U.S. patent application Ser. No. 12/234,201 by Bhaskar et al. filed Sep. 19, 2008, which is incorporated by reference as if fully set forth herein.

Figure 3:
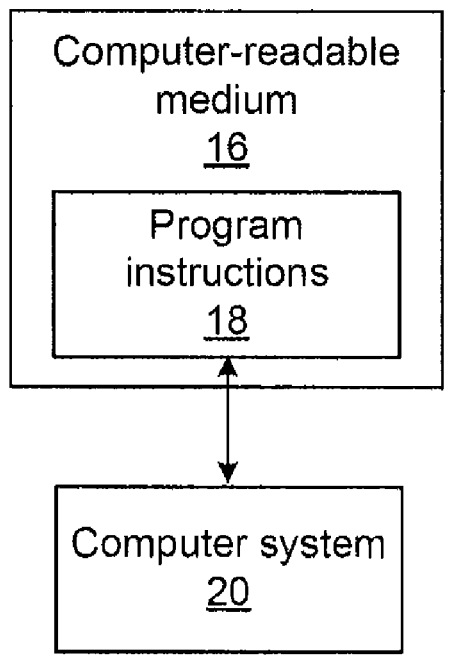
FIG. 3 is a block diagram illustrating one embodiment of a computer-readable medium that includes program instructions executable on a computer system for performing a computer-implemented method for generating an inspection process for a wafer.

Another embodiment relates to a computer-readable medium that includes program instructions executable on a computer system for performing a computer-implemented method for generating an inspection process for a wafer. One such embodiment is illustrated in FIG. 3. In particular, as shown in FIG. 3, computer-readable medium 16 includes program instructions 18 executable on computer system 20. The computer-implemented method includes separately determining a value of a local attribute for different locations within a design for a wafer based on a defect that can cause at least one type of fault mechanism at the different locations. Separately determining the value of the local attribute may be performed according to any of the embodiments described herein. The value of the local attribute may include any such values described herein. The local attribute may include any of the local attributes described herein. The different locations within the design may include any of the different locations described herein. The design may include any of the designs described herein. The at least one type of fault mechanism may include any type(s) of fault mechanisms described herein.

The computer-implemented method also includes determining a sensitivity with which defects will be reported for different locations on the wafer corresponding to the different locations within the design based on the value of the local attribute. Determining the sensitivity may be performed according to any of the embodiments described herein. The sensitivity may include any of the sensitivities described herein. The different locations on the wafer may include any of the different locations described herein. The computer-implemented method further includes generating an inspection process for the wafer based on the determined sensitivity. Generating the inspection process may be performed according to any of the embodiments described herein. The inspection process may include any of the inspection processes described herein. The computer-implemented method may include any other step(s) of any other embodiment(s) described herein.

Program instructions 18 implementing methods such as those described herein may be stored on computer-readable medium 16. The computer-readable medium may be a storage medium such as a read-only memory, a random access memory, a magnetic or optical disk, or a magnetic tape. In addition, the computer-readable medium may include any other suitable computer-readable medium known in the art.

Computer system 20 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

The computer system described above may be configured as a stand-alone system that does not form part of an inspection, metrology, review, or other tool. In such an embodiment, the computer system may be configured to send data or information to other systems (e.g., an inspection process to an inspection system) by a transmission medium that may include "wired" and/or "wireless" portions. In this manner, the transmission medium may serve as a data link between the computer system and the other system. In addition, the computer system may receive and/or acquire data from the other system via the transmission medium. In other embodiments, however, the computer system is included in an inspection system. The inspection system may be configured as described herein.

Figure 4:
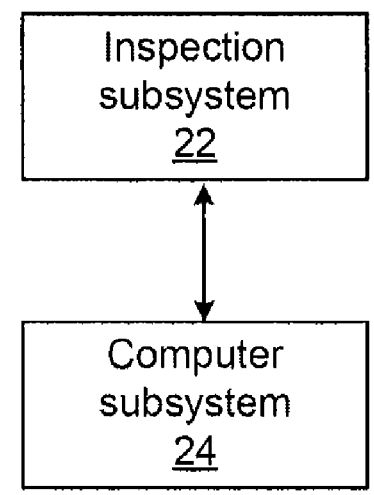
FIG. 4 is a block diagram illustrating one embodiment of a system configured to generate and perform an inspection process on a wafer.

An additional embodiment relates to a system configured to generate and perform an inspection process on a wafer. One embodiment of such a system is shown in FIG. 4. As shown in FIG. 4, the system includes computer subsystem 24. The computer subsystem is configured to separately determine a value of a local attribute for different locations within a design for a wafer based on a defect that can cause at least one type of fault mechanism at the different locations. The computer subsystem may be configured to separately determine the value of the local attribute according to any of the embodiments described herein. The value of the local attribute may include any such values described herein. The local attribute may include any of the local attributes described herein. The different locations within the design may include any of the different locations described herein. The design may include any of the designs described herein. The at least one type of fault mechanism may include any of the type(s) of fault mechanisms described herein.

The computer subsystem is also configured to determine a sensitivity with which defects will be reported for different locations on the wafer corresponding to the different locations within the design based on the value of the local attribute. The computer subsystem may be configured to determine the sensitivity according to any of the embodiments described herein. The sensitivity may include any of the sensitivities described herein. The different locations on the wafer may include any of the different locations described herein. In addition, the computer subsystem is configured to generate an inspection process for the wafer based on the determined sensitivity. The computer subsystem may be configured to generate the inspection process according to any of the embodiments described herein. The inspection process may include any of the inspection processes described herein. Furthermore, the computer subsystem may be configured to perform any step(s) of any method(s) described herein. The computer subsystem may be further configured as described above with respect to computer system 20 shown in FIG. 3.

The system also includes inspection subsystem 22 configured to perform the inspection process on the wafer. Inspection subsystem 22 may include any suitable inspection subsystem such as those included in commercially available inspection systems. Examples of commercially available inspection systems that include suitable inspection subsystems include the 2360, 2365, 2371, and 23xx systems and the Puma 90xx and 91xx series tools, which are commercially available from KLA-Tencor. In addition, the inspection subsystem may be an inspection subsystem configured for DF inspection of a wafer and/or BF inspection of a wafer. Furthermore, the inspection subsystem may be configured for patterned wafer and/or unpatterned wafer inspection. Moreover, an existing inspection system may be modified (e.g., a computer subsystem of the inspection system may be modified) such that the existing inspection system, including its inspection subsystem, can be configured and used as a system described herein. The inspection subsystem may be configured to perform the inspection process on the wafer in any suitable manner. The system may also be configured to generate results of the inspection process performed on the wafer. The results may be generated in any suitable manner and may have any suitable format. In addition, the inspection subsystem may be configured to perform any step(s) of any method(s) described herein. The embodiment of the system described above may be further configured as described herein.

Further modifications and alternative embodiments of various aspects of the invention may be apparent to those skilled in the art in view of this description. For example, methods and systems for generating an inspection process for a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for generating an inspection process for a wafer, comprising:
   separately determining a value of a local attribute for different locations within a design for a wafer based on a defect that can cause at least one type of fault mechanism at the different locations;
   determining a sensitivity with which defects will be reported for different locations on the wafer corresponding to the different locations within the design based on the value of the local attribute; and
   generating an inspection process for the wafer based on the determined sensitivity, wherein using the inspection process, defects are detected based on magnitude of a characteristic of individual output in output generated for the wafer during the inspection process and are not detected based on size of the defects.

2. The computer-implemented method of claim 1, wherein the value of the local attribute is critical radius of the defect that can cause at least one type of fault mechanism at the different locations.

3. The computer-implemented method of claim 1, wherein the value of the local attribute is determined as a function of at least one dimension of one or more features of the design at the different locations, one or more features of the design proximate to the different locations, or some combination thereof.

4. The computer-implemented method of claim 1, wherein separately determining the value of the local attribute is performed using design data for the design.

5. The computer-implemented method of claim 1, wherein separately determining the value of the local attribute is performed based on the defect that can cause the at least one type of fault mechanism at the different locations and one or more parameters of an inspection system that will perform the inspection process.

6. The computer-implemented method of claim 1, wherein the different locations span an entirety of the design.

7. The computer-implemented method of claim 1, wherein the value of the local attribute has an inverse relationship to the sensitivity.

8. The computer-implemented method of claim 1, wherein the determined sensitivity is different than a sensitivity with which defects will be detected at the different locations on the wafer.

9. The computer-implemented method of claim 1, wherein the sensitivity is the sensitivity with which the defects will be detected at the different locations on the wafer and reported for the different locations on the wafer.

10. The computer-implemented method of claim 1, wherein the sensitivity is a sensitivity to the magnitude of the characteristic of the individual output in the output generated for the wafer during the inspection process.

11. The computer-implemented method of claim 1, further comprising generating a map of the values of the local attribute as a function of the different locations within the design, wherein determining the sensitivity is performed using the map.

12. The computer-implemented method of claim 1, wherein determining the sensitivity comprises generating a map of the sensitivities with which the defects will be reported for the different locations on the wafer as a function of the different locations within the design.

13. The computer-implemented method of claim 1, wherein determining the sensitivity comprises assigning the different locations within the design to different groups based on the value of the local attribute thereby assigning the different locations on the wafer corresponding to the different locations within the design that will have at least similar noise statistics to the same group.

14. The computer-implemented method of claim 1, wherein determining the sensitivity comprises assigning the different locations within the design to different segments based on the value of the local attribute and separately estimating noise statistics for the different segments, and wherein the noise statistics are noise statistics for the output that would be generated during the inspection process at the different locations on the wafer corresponding to the different locations within the design assigned to the different segments.

15. The computer-implemented method of claim 1, wherein determining the sensitivity comprises assigning the different locations within the design to different segments based on the value of the local attribute, separately estimating noise statistics for the different segments, and determining the sensitivity for the different segments based on the noise statistics, and wherein the noise statistics are noise statistics for the output that would be generated during the inspection process at the different locations on the wafer corresponding to the different locations within the design assigned to the different segments.

16. The computer-implemented method of claim 1, wherein determining the sensitivity comprises assigning different portions of an entire range of values of the local attribute to different segments, separately determining different sensitivities for the different segments based on the values of the local attribute in the different portions assigned to the different segments, and separately assigning the different locations within the design to the different segments based on the different portions in which the values of the local attribute determined for the different locations fall.

17. The computer-implemented method of claim 1, wherein determining the sensitivity comprises assigning different portions of an entire range of values of the local attribute to different segments, separately determining different sensitivities for the different segments based on the values of the local attribute in the different portions assigned to the different segments, and generating a map of the sensitivities with which the defects will be reported for the different locations on the wafer as a function of the different locations within the design based on the value of the local attribute for the different locations, the different portions of the entire range of the values of the local attribute assigned to the different segments, and the different sensitivities determined for the different segments.

18. The computer-implemented method of claim 1, further comprising separately determining a value of a local image attribute for the different locations on the wafer based on the output generated for the wafer by an inspection system during the inspection process, wherein determining the sensitivity is performed based on the values of the local attribute and the local image attribute.

19. The computer-implemented method of claim 1, further comprising separately determining a value of a local image attribute for the different locations on the wafer based on the output generated for the wafer by an inspection system during the inspection process, wherein determining the sensitivity is performed based on the value of the local attribute, the value of the local image attribute, and coordinate inaccuracy of the inspection system.

20. The computer-implemented method of claim 1, wherein determining the sensitivity is performed based on the value of the local attribute and information about hot spots in the design.

21. The computer-implemented method of claim 1, wherein the value of the local attribute does not indicate if the different locations within the design are hot spots in the design, and wherein determining the sensitivity is not performed based on information about the hot spots in the design.

22. The computer-implemented method of claim 1, wherein the design printed on the wafer cannot be resolved by an inspection system that performs the inspection process.

23. The computer-implemented method of claim 1, wherein separately determining the value of the local attribute and determining the sensitivity are performed before defects are detected on the wafer in the inspection process.

24. The computer-implemented method of claim 1, wherein separately determining the value of the loca attribute and determining the sensitivity are performed, offline.

25. The computer-implemented method of claim 1, wherein using the inspection process, the defects are reported based on the magnitude of the characteristic of the individual output in the output generated for the wafer during the inspection process and are not reported based on the size of the defects.

26. The computer-implemented method of claim 1, wherein the inspection process comprises determining a position of the output generated for the wafer by an inspection system during the inspection process in design data space such that the output generated at the different locations on the wafer corresponding to the different locations within the design can be identified.

27. A computer-readable medium, comprising program instructions executable on a computer system for performing a computer-implemented method for generating an inspection process for a wafer, wherein the computer-implemented method comprises:
  separately determining a value of a local attribute for different locations within a design for a wafer based on a defect that can cause at least one type of fault mechanism at the different locations;
  determining a sensitivity with which defects will be reported for different locations on the wafer corresponding to the different locations within the design based on the value of the local attribute; and
  generating an inspection process for the wafer based on the determined sensitivity, wherein using the inspection process, defects are detected based on magnitude of a characteristic of individual output in output generated for the wafer during the inspection process and are not detected based on size of the defects.

28. A system configured to generate and perform an inspection process on a wafer, comprising:
  a computer subsystem configured to:
    separately determine a value of a local attribute for different locations within a design for a wafer based on a defect that can cause at least one type of fault mechanism at the different locations;
    determine a sensitivity with which defects will be reported for different locations on the wafer corresponding to the different locations within the design based on the value of the local attribute; and generate an inspection process for the wafer based on the determined sensitivity; and an inspection subsystem configured to perform the inspection process on the wafer, wherein using the inspection process defects are detected based on magnitude of a characteristic of individual output in output generated for the wafer during the inspection process and are not detected based on size of the defects.

* * * * *